United States Patent [19]
Bichon et al.

[11] Patent Number: 4,888,398
[45] Date of Patent: Dec. 19, 1989

[54] BIODEGRADABLE POLYPEPTIDE AND THE USE THEREOF FOR THE GRADUAL RELEASE OF DRUGS

[75] Inventors: Daniel Bichon, Gaillard, France; Bernard Lamy, Carouge, Switzerland

[73] Assignee: Battelle Memorial Institute, Geneva, Switzerland

[21] Appl. No.: 788,408

[22] Filed: Oct. 17, 1985

[30] Foreign Application Priority Data

Oct. 19, 1984 [CH] Switzerland .................. 5021/84-9

[51] Int. Cl.$^4$ .................. C08G 69/08; A61K 9/52
[52] U.S. Cl. .................. 525/420; 525/419; 528/328; 528/329.1
[58] Field of Search .................. 528/328, 329.1; 530/300, 324, 350; 424/19, 21, 31, 32, 36; 525/419, 420

[56] References Cited

U.S. PATENT DOCUMENTS

| 3,867,352 | 2/1975 | Akamatsu et al. | 528/325 |
| 4,161,948 | 7/1979 | Bichon | 427/2 |
| 4,450,150 | 5/1984 | Sidman | 424/14 |

Primary Examiner—Morton Foelak
Assistant Examiner—Nathan M. Nutter
Attorney, Agent, or Firm—Cushman, Darby & Cushman

[57] ABSTRACT

Biodegradable alkyloxycarbonylmethyl or aryloxycarbonylmethyl polyaspartate and polyglutamate which can be used as a carrier for drugs which are either in the encapsulated state or are incorporated in the polymer matrix. The polypeptide thus loaded degrades enzymatically in the organ where it has been placed and thus gradually releases the drug which it contains.

7 Claims, No Drawings

BIODEGRADABLE POLYPEPTIDE AND THE USE THEREOF FOR THE GRADUAL RELEASE OF DRUGS

BACKGROUND OF THE INVENTION

1. Field of the Invention

The present invention relates to a new biodegradable esterified polypeptide in which drugs can be incorporated, the drugs then being released gradually as biochemical degradation of the polymer proceeds.

2. Description of the Prior Art

Non-toxic biodegradable polymers which can be used as a reservoir for drugs and permit the controlled progressive release thereof into the organism during degradation of the carrier polymer have been known for several years. General information about such products is found in the work: "Fundamental Aspects of Biocompatibility" by D. F. Williams, CRC Press (1981), and also U.S. Pat. No. 4,093,709.

These polymers include, more particularly, synthetic polypeptides (polyamino acids) in which the structure is close to that of proteins. These polypeptides are biocompatible and their degradation products (amino acids) can be absorbed by the organism. Thus, Sidman et al (J. Membr. Sci (1980), Vol. 7(3), pp. 277-91) have disclosed a copolymer of glutamic acid and ethyl γ-glutamate in which the degradation rate is dependent on the composition of the copolymer (molar ratios of esterified segments to non-esterified segments) and which allows numerous medicinal products, in particular steroids, peptides, anti-malaria products, anti-cancer products and others to be stored. Such polymers can be used in the form of rods containing the desired drug in a mixture or in the form of capsules containing the drug if the drug is immiscible with the polymer. Furthermore, alkyl polyglutamates and polyaspartates (simple esters of these polyacids) are not degradable within the prescribed time (of a value compatible with their pharmaceutical use) unless they are in a partially hydrolysed form (Asano et al; J. Macromol. Sci. Chem. A21 (5) (1984), pp. 561-582). To obtain such partially esterified polymers, it is necessary to subject these polyglutamates or polyaspartates to a controlled hydrolysis reaction in which the conditions are very difficult to reproduce. Moreover, very slight differences in the degree of hydrolysis have a considerable influence on the subsequent rate of biodegradability and this constitutes an additional problem with the use of these polymers for the above-mentioned purposes.

Thus, in spite of the value of the foregoing products, there have still been attempts to find a product having improved qualities and, in particular, having the following properties:

1. Excellent solubility in the majority of conventional non-toxic solvents used in drugs (in fact the known derivatives of polyamino acids are generally soluble only in certain special solvents (DMF, pyridine, $F_3CCOOH$) which are unsuitable for use in pharmaceutical products).

2. Capacity for shaping under heat. In fact, currently known synthetic polypeptides cannot generally be mixed with the usual biocompatible plasticizers (polyalkylene glycols) and they are not therefore thermoplastic.

3. Improved control of the degradation process. In fact, the rate of degradation of known synthetic polypeptides is linked to their chemical structure in a manner which is difficult to reproduce and, in particular, to the esterification rate. Thus, in a given case (Sidman K. R., et al., PB 81-132136 NTIS (1980), page 42) a variation in the esterification rate of the order of 10% causes the degradation rate to pass from 1 to one hundred fold (Sidman et al.).

The polymer according to the invention has enabled these improvements to be made. It is an esterified polypeptide corresponding to the formula:

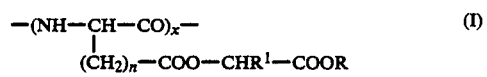

in which $R^1$ is a lower alkyl or hydrogen, in which R represents a substituted or unsubstituted aliphatic or aromatic radical (in particular a hydroxylated or alkoxylated polyoxyalkylene radical) or $R^1$ and R, bound to one another, form, by means of the —COO— group a lactone ring having 5 or 6 bonds, where n is 1 or 2 and x is such that the molecular weight is at least 5000 D.

As seen from formula (I), the polymer according to the invention is a polyaspartate or polyglutamate esterified by a hydroxyacetic (lactic or glycolic) ester (HO—$CHR^1$—COOR) in which R is either any organic radical or a group connected to $R^1$ so as to form a ring. The term "any" implies that the nature and structure of the group R is not critical and that, for the moment, no cases have been found in which, when R forms part of known compounds which can be esterified by lactic derivatives, the corresponding compound according to the invention cannot be obtained. However, it is preferable to use compounds in which R represents a substituted or unsubstituted aliphatic, alicyclic, aromatic or alkylaromatic group, the substituents being selected from the biocompatible functional organic groups. The preferred groups R include the methyl, ethyl, propyl, isopropyl, isobutyl, tert-butyl, neopentyl, phenyl, and benzyl groups, the alkyls of $C_{10}$ to $C_{22}$ fatty alcohols and other similar groups, and the methoxylated polyoxyethylene glycol containing from 1 to 100 oxyethylene units. Other compounds are obviously possible, but the inventor has not been able to consider all.

When R and $R^1$ are bound together to produce a saturated or unsaturated carbon-carbon bond, these carbon atoms may or may not be substituted by aliphatic or aromatic radicals. Some non-limiting examples of these substituted or unsubstituted ester-lactone groups

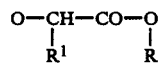

corresponding to the foregoing definition: dimethylene group —$CH_2$—$CH_2$—; dimethylethylene group —$CH(CH_3)$—$CH(CH_3)$—; vinylene group —CH═CH—; trimethylene group —$(CH_2)_3$—; methenylethylene group —CH═CH—$CH_2$—, 1,2-phenylene group

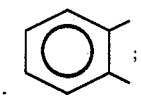

cyclohexenylene

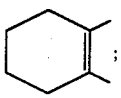

cyclopentenylene group

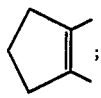

cyclopentadienylene

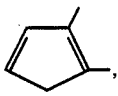

group corresponding to the formula

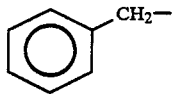

and others.

The polymer according to the invention can also be present in the form of a copolymer with other polyamino acids. In this case, the copolymer will have the formula:

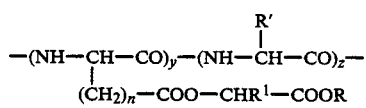

in which R' is any non-carboxylated or carboxylated amino acid radical; if it is carboxylated, the COOH groups may be free partially esterified or totally esterified groups, and the R' groups of the —(NH—CH-R'—CO) units can be identical or different in the copolymer chain wherein $y+z=x$, the value of x always being selected so that the copolymer has an average molecular weight of at least 5000 D. Of course, if R' is identical to the group —(CH$_2$)$_n$—COO—CR$^1$-R$^2$—COOR, but with different n (one of them being 1 and the other 2) an esterified copolymer of glutamic and aspartic acid will be present. Generally speaking, however, R' preferably has different groups such as methyl (alanine), isopropyl (valine), isobutyl (leucine and isoleucine), benzyl (phenylalanine), etc. In principle, any other amino acids can also be used although it has not been possible to test all of them. R' can also represent a glutamic or aspartic acid radical which is non-esterified or esterified partially by any alcohol, for example, MeOH or EtOH, that is, for example —(CH$_2$)$_n$—COOH or —(CH$_2$)$_n$—COOMe. It should be noted that if R' represents a free glutamic or aspartic acid radical, the polymer can be represented by formula I providing that the degree of substitution (esterification) is less than 100%. This case can obviously also be represented by formula II in which R'=(CH$_2$)$_n$—COOH and y/z+y being equal to the degree of substitution.

It is also possible to have amino acids from the L or D series without discrimination. The amino acids of the L series (or natural amino acids) are of particular interest because the polypeptides containing them can be degraded by enzymes (proteases) in the human body whereas the polypeptides constituted by D units can not. This difference can be utilised with copolymers containing D and L amino acids so as to provide polymers in which the degradation rate is modified.

Returning to more general considerations, it should be noted that the molar ratio in copolymer II of the other free or partially esterified polyamino acid also allows the rate of biodegradation of the copolymer to be adjusted to a significant extent as a function of the agents present in the organism at the destination of the mixture of copolymer and drug to be administered (that is to say in the organ where the drug is to act). Thus, for example, if the copolymer is a copolymer of polyglutamate I and leucine, the molar ratio between the two constituents will be selected as a function of the relative degradation rate at the location under consideration of the polyglutamate and the polyleucine. Generally speaking, the z/y ratio can vary from 1 to 30, but these limits can be exceeded if necessary. Of course, if the group R' does not represent a group of a single type in the copolymer chain, that is to say, for example, if one of the R' represents a free amino acid radical and another R' represents an esterified amino acid radical, the variations of R' could be designated by the symbols R'', R''', etc. for convenience. The general formula of such a copolymer can thus be shown as follows:

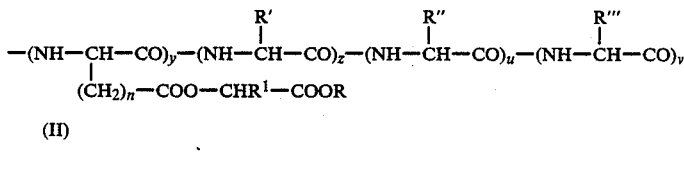

wherein the sum of y, z, u, v, ..., etc. is equal to x; u, v etc. can obviously be zero if the radical designated by R' is of a single type. A typical case where the copolymer has distinct R' and R'' arises when these groups represent esterified and non-esterified glutamic and/or aspartic acid radicals, the schematic formula for such a polymer (which is partially methylated in the case under consideration) being represented as follows:

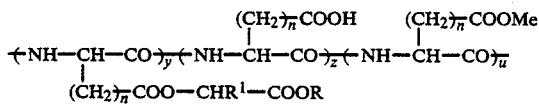

The nature of the group R can also influence the degradation rate of polymer I. Thus, for example, if R is a large or bulky group (for example tert-butyl), degradation will be slower than with a methyl or ethyl group.

It is obvious that, from the point of view of optical isomerism, the polymers according to the invention can comprise elements having a L or D configuration or racemic mixtures or polymers in which one of the configurations dominates. The biochemical properties of these various combinations are obviously not identical, the polymers in which the natural forms (L) dominate being more accessible to enzymatic degradation. The degradability can thus be controlled by controlling the relative proportions of each form in the copolymer.

The polymers I and copolymer II are insoluble in water and generally soluble in one or more of the conventional solvents such as acetone, ethylmethyl ketone (EMK), tetrahydrofuran (THF), dioxan, ethylacetate, monoglyme, diglyme and others, allowing polymers I and copolymer II to be converted easily into balls, rods, fibres, filaments, microcapsules, films etc. Polymers I and II may be insoluble or soluble in chlorinated solvents, for example chloroform, depending on their structure. Insolubility in chloroform can sometimes be overcome by adding acetone. This ability to dissolve the polymers I and II in numerous solvents which are miscible or immiscible with water also renders them directly compatible with numerous drugs which are liquid or soluble in the same solvents. Thus, for example to encapsulate a watersoluble product in micro-balls of polymer, it is possible to disperse an aqueous solution of the drug in a solution of polymer, the polymer solution containing a solvent which is immiscible with water, then evaporating this solvent so as to form the solid capsules of polymer.

In addition, depending on its structure and, more particularly, if R is a branched group, for example t.Bu, polymer I is frequently compatible with the polyalkylene glycols (polyethylene glycol and polypropylene glycol), allowing these glycol polyethers to be used as plasticizers for polymer I and thus to provide a homogeneous mixture having a low melting point. It will be observed that, when using PEG as solvent for the polymer according to the invention, the polymer will have a certain moisture content of the order of from 5 to 50% by weight enabling the mixture to be homogenized better. An entire range of thermolabile drugs can easily be incorporated into such a mixture (melting at temperatures of the order of from 40° to 60° C.) in order to obtain granulates or microcapsules Furthermore, the presence of very hydrophilic polyalkylene glycols allows the sensitivity of the polymer and the copolymer towards aqueous biological liquids to be increased and their enzymatic degradation in situ to be simplified. It should be noted that the known synthetic polypeptides do not have these favourable properties of solubility and compatibility with the PEG. Thus, for example, to form films of polyglutamic acid having significant mechanical strength and a certain insolubility in water, it is necessary to use solutions in solvents which are relatively difficult to handle and are not used in pharmaceutical preparations such as dimethylformamide (DMF) and dichloroacetic acid (DCA) and trifluoroacetic acid (TFA). The films of polyglutamic acid obtained from aqueous solutions (at pH 7.4, that is to say where the salt of the acid is formed at least in part) have no mechanical strength and are rapidly dissolved in water, rendering the polymer completely unsuitable as a retard drug support in the sense of the present invention. The same rationale applies to mixtures of polyglutamic acid and polyethylene glycol which are instantly soluble in water. When the group R represents a fatty alcohol radical, for example a $C_{12}$ or higher alkyl radical, the polymer is soluble in chlorinated solvents and the esters, for example ethyl acetate. It is also oil-soluble even if the degree of substitution is not very high, for example 50% (see formula II in which $R=C_{12}$ alkyl and $R'=(CH_2)_n-COOH$ wherein $z=y$). It is thus possible to form viscous or pasty solutions in oils such as sesame oil or isopropyl myristate, and these solutions form stable emulsions with water. Emulsions of this type allow intra-muscular injection of lipophilic drugs (dissolved in the polymer solution) of which the release time can be controlled as a function of the quantity of said polymer in solution.

The biodegradation of polymer I can be shown as follows:

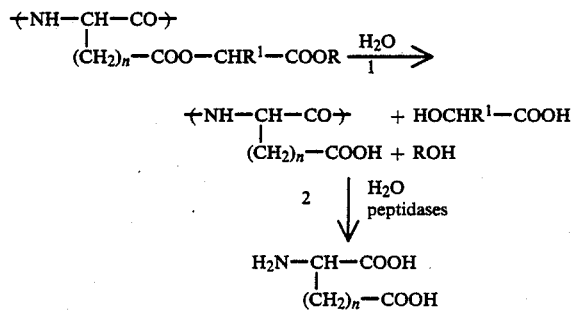

Reaction (2) follows reaction (1) and, therefore, the higher the hydrolysis rate of the lactone or hydroxy acetic ester, the faster the biodegradation of the polymer. It should be noted that when $R^1$ is a methyl, the compound resulting from reaction (1) is lactic acid, a biologically compatible product. The higher the degree of esterification, that is to say the greater it is with respect to z in formula II in which $R'=(CH_2)_n-COOH$, the slower the degradation of the polymer, as can be deduced from the foregoing reaction diagram. The products resulting from reaction (1) when R and $R^1$ are bound to one another are also very advantageous owing to their negligible toxicity. Thus, if the combination $R-R^1$ corresponds to the ethylene or 1,2-phenylene groups, the degradation products will be the vinyl hydroxy acetic and phenyl hydroxyacetic acids respectively which are slowly eliminated by the organism without secondary reactions.

Polymer I can be prepared by direct esterification of a salt of the corresponding polyamino acid with an α-halogenated acetic ester ($X-CHR^1-COOR$ (III)) in which X can be chlorine, bromine or iodine. The salt of polyamino acid is preferably a tertiary amine salt (for example tributylamine or triethylamine). A method of this type is shown in E. Falch et al., J. Med. Chem. (1981) Vol. 24 , pp. 285–289.

The polyamino acid or copolyamino acid, esterification which produces polymer I or copolymer II, is easily obtained by conventional means involving esterification by a lower alcohol of the lateral carboxyl of an acid corresponding to the formula

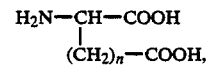

the transformation of the ester into corresponding N-carboxyanhydride (NCA) by phosgene in a dioxan or THF medium, polymerization of the NCA into esterified polyamino acid and hydrolysis of the protective ester group in an alkaline medium or by trifluoroacetic acid. Such methods are know (Encyclopedia of Polymer Science and Technology; N-carboxyanhydrides, Vol. II, page 837). If a copolymer in which R' represents a partially esterified lateral carboxyl group ($R' = -(CH_2)_n-COOH$ and $R'' = -(CH_2)_n-COOAlk$) is desired, hydrolysis of the protective ester group will be only partial. Thus, for example, the starting product to be esterified with the compound $XCHR^1-COOR$ will be a copolymer of $H_2N-CH[(CH_2)_n-COOH]-COOH$ acid and $NH_2-CH[(CH_2)_n-COO\ Alk]-COOH$ ester.

The polymers and copolymers according to the present invention are biodegradable and biocompatible when used for the slow and controlled release of drugs, for example from thin films prepared by pouring a solution of polymer and drug onto a support then drying them by evaporation of the solvents of the solution. Methods of this type are described in "Controlled Release of Macromolecules from Polymers" by R. Langer et al., Biomedical Polymers, Ed. Goldberg and Nakajima, Academic Press, 1980). After drying the film, the drug may be dissolved or in the form of a suspension of particles.

Owing to their solubility in PEG, some of the polymers according to the invention can be plasticized by the addition of a small quantity of this polyol. The thermoplastic properties enable the polymers to be moulded under heat into various shapes, for example strands, capsules, implants, which are very economical to produce.

Furthermore, such mixtures with PEG enable the rate of biodissolution of the polymer in the organism to be adjusted as a function of the content of PEG and of its molecular weight and, consequently, the rate of release of the incorporated drugs. In addition, the dissolving power of such polymer PEG mixtures with respect to drugs is considerable and allows the drugs to be incorporated in exceptionally high concentrations.

Polymer I and copolymer II can be used as reservoir for drugs in various ways. Thus, for example, the present polymers I and copolymers II can be used to produce microcapsules containing a drug. Microcapsules of this type comprise a polymeric membrane and contain an aqueous or oily solution in which the drug is suspended or dissolved. Microspheres, that is to say solid particles or balls containing the drug in the dispersed state or in the state of a solid solution in the polymer matrix can also be produced. Microporous products known as microsponges can also be produced. In general, any methods for producing retard drugs, that is to say having the property of releasing the drug in a prolonged manner as degradation of the support proceeds can be employed using the present polymers. A description of these methods will be found in the following works "Biodegradables and Delivery Systems for Contraception", Mafex E.S.E, MTP Press Limited (1980), "Controlled Release Technologies - Methods, Theory and Applications" Vol 1 and 11, A. F. Kydonieus, CRC Press (1980) and "Microencapsulation - New Techniques and Applications" by Tamotsu Kondo, Techno Inc. (1979) Japan. The solubility of the present polymers in numerous solvents which are miscible or immiscible with water is an advantage for their application according to the methods described in these references. It is also possible to prepare threads constituted by these polymers by extruding a solution thereof in a die and by precipitating the thread either by evaporation or by a bath of non-solvent by conventional spinning methods. The prepared filaments can thus be knitted, knotted or woven to form sutures, ligatures, or tubular structures which can be used as artificial ateries, veins, conduits or internal organs for temporary use. The polymers according to the invention can also be used, either directly or mixed with a plasticiser, for the manufacture of films or surgical prosthesis which are used, for example, for consolidating fractured bones such as hooks, needles, screws, reinforcing plates, pads etc., and these materials can be produced by pouring or moulding a solution, shaping under heat or by machining solid blocks of polymer. Such prosthesis can be absorbed so they are gradually eliminated in the organism and it is not necessary to carry out a new operation to remove the reinforcing and consolidating material as is the case nowadays.

The polymers and copolymers according to the invention can also be used for preparing biodegradable surgical dressings. Dressings of this type are constituted by one or more successive layers obtained from solutions of these polymers in a water-compatible solvent deposited on a support and solidified by extraction of the solvent under consideration in water. Extraction of this type can be carried out by placing the solution in contact with water, for example by washing or immersion.

Dressings of this type can be formed by pouring solutions on a support (these solutions containing or not containing one or more drugs, for example a disinfectant) under sterile conditions while treating the entire mixture with water then detaching the undissolved film of the support and drying it before use, if necessary, (or while packaging it under sterile conditions if it is not proposed for immediate use).

It is also possible, in an advantageous embodiment, particularly in the case of solutions of the present polymer in which R is a branched radical or fatty alkyl in PEG, to pour one or more solutions (in the form of viscous liquids or ointments) directly onto the wound to be dressed and then, as above, to solidify (insolubilize) the dressing by treating the dressed region with water (spraying, immersion of the dressed limb in a water bath or other treatment). A method of this type provides an excellent seal between the wound and the external air and minimizes the risks of infection. Furthermore, in view of the biodegradability of the dressing film, it is not necessary to allow for its removal, as it is resorbed in conjunction with healing.

Of course, the exact composition of the polymer or copolymer used should be adjusted as a function of the degradation rates and the characteristics of absorption in vivo, depending on the nature of the prosthesis under consideration.

The following Examples illustrate the invention.

EXAMPLE 1

Tert-butyloxycarbonylmethyl polyglutamate

Polyglutamic acid (PGA) was prepared from N-carboxyanhydride of methyl γ-glutamate dissolved in methylene chloride. Triethylamine was used as polymerization initiator (A/I=100). The polymer ws then precipitated by the addition of methanol and then dried under vacuum. The solid was redissolved in trifluoroacetic acid (TFA) so as to produce a 5% by weight solution, and a volume of distilled water sufficient for the final solution to contain equal volumes of water and TFA was added dropwise while stirring vigorously. The mixture was stirred for a further 24 hours at ambient temperature (viscous solution) after which the entire mixture was poured over distilled water in a large excess, leading to precipitation of the polyglutamic acid.

This acid was filtered and dried. The purity of the acid thus obtained was determined by NMR analysis in TFA (absence of the methylester band —O—CH$_3$ at 4.5 ppm).

2.5 g of polyglutamic acid (0.019 moles, relative viscosity measured 2.6) was dissolved in 100 ml of dimethylformamide (DMF), then 3.78 g (0.019 moles) of tributylamine and 3.7 g of tert-butyl α-bromoacetate were addeded successively. After stirring for 24 hours, the mixture was diluted with acidified water (HCl 0.05 M), causing the desired polymer to precipitate. The polymer was redissolved in 200 ml of acetone and was then re-precipitated by dilution in 3 l of 0.05 M HCl. This purification treatment was then repeated by re-dissolution in 200 ml of acetone and precipitation under ether. After drying, 2 g (43%) of the polymer corresponding to the formula

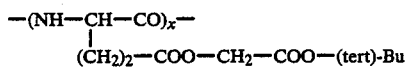

was obtained.

NMR analysis in trifluoroacetic acid (TFA) yielded the following data: σ (t.butyl) 1.35 ppm, 9H; σ 2–3 ppm, —CH$_2$— α and β; σ 5 ppm 3H, α —CH and O—CH$_2$—CO; σ=8 ppm 1H, —NH—. By integration, it was found that the polymer was 75% esterified. Consequently, the product thus obtained could be represented by formula II below

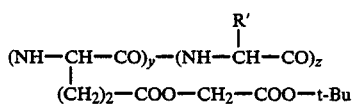

In which R' is a (CH$_2$)$_2$—COOH radical and y=3z. This polymer is soluble in the following solvents: acetone, THF, DMF, polyethylene glycol (PEG-400). It forms gels which are insoluble in chlorinated solvents and benzene. It should be noted that, for good dissolution in PEG, the present polymer should not be completely dried but should maintain a certain residual moisture content after purification (for example from 5 to 50% by weight). A completely dry polymer cannot be redissolved directly in PEG. It first has to be dissolved in TFA and re-precipitated, for example with water. It will be noted that the degree of esterification of the —COOH group (75% in the present case) can be modified as a function of the quantity of α-bromoacetate used. Thus, with 0.5 equivalent of this reagent, the degree of substitution is approximately 30% whereas 85% of substitution is obtained with 2 equivalents.

If polyglutamic acid is replaced by polyaspartic acid in the foregoing example, the corresponding polyaspartate is obtained, of which the properties are similar.

EXAMPLE 2

2-hydroxybutyrolactone polyglutamate

The process used in Example 1 was followed, starting with 2 g of polyglutamic acid (PGA), 35 ml of DMF, 5.74 g of tributylamine (2 equivalents), 5 g of H$_2$O and 5.12 g of α-bromobutyrolactone. After stirring for 4 days, the mixture was precipitated with water, redissolved with DMF and re-precipitated with ether. After drying, IR analysis in KBR produced the following results: ν$_{(CO)}$, 1760 cm$^{-1}$ (lactonic carbonyl); ν$_{(CO)}$, 1720 cm$^{-1}$ (carboxylic carbonyl). The polymer dissolves in 0.1 N caustic soda from which it can be titrated in the reverse direction by 0.1 N HCl (turn to pH 2–3). Titration corresponds to the reformation of hydroxycarboxylic polyglutamic ester IIC below from the corresponding sodium salt, itself resulting from the opening of the lactone ring by dissolution in the soda of the desired polymer IIB. The acid IIC is a fairly strong acid (pK∼1) which slowly reforms the starting lactone in water to pH 2–3 (see diagram below).

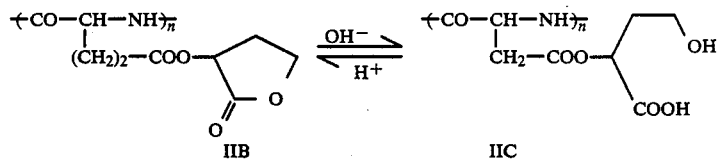

2-hydroxybutyrolactone polyglutamate is soluble in the following solvents: DMF, TFA, dichloroacetic acid (DCA). It is insoluble in the following solvents: acetone, chloroform, methanol, water.

EXAMPLE 3

α-hydroxyvalerolactone polyglutamate

The process adopted in the preceding Examples was followed, starting from 1 g of PGA (7.8 mMoles), 40 ml of DMF, 2.87 g (15.5 mMoles) and 2.77 g (15.5 mMoles) of α-bromo-γ-valerolactone. After stirring for 48 hours at ambient temperature, the polymer was precipitated by dilution in water, and was then redissolved in acetone and re-precipitated under ether. NMR analysis demonstrated, by integration of the peaks corresponding to the amino proton (σ=8 ppm) and to the protons CH—CH$_3$ (σ=0.35 ppm) that the degree of esterification was approximately 90%.

The IR spectrum confirms the presence of the lactonic peak (ν$_{(CO)}$=1760 cm$^{-1}$).

The product corresponding to the formula

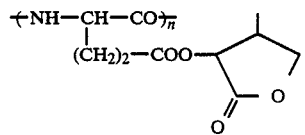

is soluble in the following solvents: TFA, DMF, acetone, CHCl$_3$, CH$_2$Cl$_2$, etc., and insoluble in the following solvents: EtOH, MeOH, ethylmethyl ketone (EMK), 2-methoxyethyl acetate (MEA), ethylacetate.

EXAMPLE 4

Methoxycarbonylmethyl polyglutamate

The process described in the preceding Examples was followed, starting from 1 equivalent of each of the following reagents. The mixture being in a quantity of solvent (DMF) corresponding to 50 parts of PGA: PGA; Bu$_3$N; BrCH$_2$—COOMe. The product corresponding to the formula

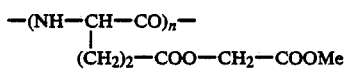

was thus obtained with a yield of 60% and having the following properties: solubility in the following solvents: acetone, THF, dioxan, DMF. The solubility is imperfect in pure PEG 400. Opalescent quasi-solutions having a tendency to form gels are obtained in this case. The polymer swells but does not dissolve in the presence of lower alcohols.

EXAMPLES 5 to 8

The procedure from the preceding Examples was repeated starting from PGA (1 equivalent) and the halogenated compounds (1 equivalent) shown in the following table, while stirring for 48 to 100 hours in DMF at ambient temperature. The products were purified by redissolution and re-precipitation as described above.

| Example | Halogenated Ester | Product obtained = polyglutamate of |
|---|---|---|
| 5 | BrCH$_2$—COOEt | -ethoxy-carbonylmethyl |
| 6 | BrCH$_2$—COOBz | -benzyloxycarbonylmethyl |
| 7 | BrCH$_2$—COOPh | -phenoxycarbonylmethyl |
| 8 | BrCH(CH$_3$)—COOMe | -methoxycarbonyl-1-ethyl |

The properties of solubility of these products are as follows:

| Example | Solvents | Non-solvents |
|---|---|---|
| 5 | acetone, dioxan, THF, DMF | CHCl$_3$, CH$_2$Cl$_2$, Bz |
| 6 | acetone, AcOEt, CHCl$_3$, dioxan | Bz |
| 7 | acetone, dioxan THF, DMF | chlorinated solvents |
| 8 | as in Example 5 | as in Example 5 |

EXAMPLE 9

Copolymer of tert-butoxycarbonylmethyl polyglutamate and leucine (50:50)

This copolymer was prepared in a manner similar to that described in Example 1, but using as starting product, instead of polyglutamic acid, a statistic copolymer (50:50 by weight) of L-leucine and L-glutamic acid, itself prepared by copolymerisation of the corresponding N-carboxy anhydrides. The structure of the copolymer obtained has been established by the conventional methods of analysis (IR and NMR spectra). Thin films (0.1 mm) of this polymer were prepared by spreading a layer of its (10% by weight) acetone solution on a glass plate and by evaporating the solvent. These films were then subjected to degradation in a protease solution in the company of similar films prepared from the polymer of Example 1. It has been found that the degradation of the copolymer films was slower than that of the films of the polymer alone.

EXAMPLE 10

Copolymer of methoxycarbonylmethyl polyaspartate and leucine

The method described above was followed, but using as starting product a copolymer of aspartic acid and leucine obtained in a similar manner. A tert-butoxy carbonylmethyl polyaspartate was also prepared by the method according to Example 1 by way of comparison. The properties of these polymers and copolymers were very similar to those of the corresponding glutamic polymers.

EXAMPLE 11

30 ml of PEG-400 (Ph. Helv. IV) were added to a solution of 2 g of the polymer according to Example 1 in 300 ml of acetone and this solution was subjected to evaporation under vacuum until a very viscous solution having the consistency of an ointment was formed, (600–700 P). A layer of approximately 0.2–0.5 mm of this paste was spread on a wound made in the skin of an experimental rat, and sterile water was sprayed on the covered region for two minutes. A flexible and strong film perfectly matching the shape of the wound and not exhibiting any visible cracks after 24 hours despite the movements of the treated animal was formed. A film of this type, obtained on an inert support (glass plate) by identical methods, exhibits steam permeability at ambient temperature of 4 mg/h.cm$^2$.

After two weeks, it was found that the wound had healed perfectly, the protective film for its part having been absorbed.

EXAMPLE 12

Production of a biodegradable implant containing a releasable drug 1 g of the polymer according to Example 1 and 1 g of Diazepam (Roche) were dissolved in a mixture of 200 ml of PEG-400 and 50 ml of 2-methoxyethyl acetate. This solution was subjected to slow evaporation under normal pressure, then under reduced pressure (1 Torr; 40° C.) until a pasty product was obtained and was then extruded in strands of 0.9 mm in a die (20 bar; 60° C.).

This paste was studied by differential scanning calorimetry (DSC) and it was found, by the absence of peaks corresponding to fusion (130° C.) of the Diazepam, that a real solution had been found. It should be noted in this context that by omitting PEG from the starting solution, a product having a similar appearance but which is not extrudable under the above-mentioned conditions and contains Diazepam in the partially crystallized state is obtained after evaporation.

After cooling the thread at −5° C. in order to increase its rigidity, a 5 cm fragment (32 mg, 14.5 mg of drug) was introduced into the needle (1 mm φ) of an injection syringe. This section was then injected (implanted) beneath the skin of a laboratory rat (male Wistar, 350 g). To do this, the needle was introduced beneath the skin of the animal over a length slightly greater than that of the section to be implanted, then the needle was withdrawn while pressing on the plunger of the syringe so that the fragment of thread remains in position as the needle is withdrawn.

Samples of blood were then taken from the animal periodically and were analysed by GPC (gaseous phase chromatography according to I. A. Zingales (J. of Chromatography Vol. 75 (1973), pp. 57-59) to determine the Diazepam content. A Hewlett-Packard 5710-A chromatogram, a Supelco SP-2250 column and an electron capture detector were used. These analyses demonstrated that the plasma concentration of Diazepam tends to a maximum (after 48 h) of 1800 ng/ml, then slowly drops to 100 to 200 ng/ml after 10 days. In this connection, it is found that, to be effective from the point of view of pharmaceutical dynamics, such a concentration should be between 180 ng and 3 μg/ml, depending on the desired effect.

As the present experiment was carried out on several animals, some of them were sacrificed at different times after implantation and it was found that after 12 days the implant substance was highly degraded and was being absorbed by the adjacent tissues.

It will also be noted by way of comparison that after subcutaneous injection of Diazepam in an aqueous alcoholic solution according to the normal practice, the effect of the drug lasted only 5 hours approximately.

EXAMPLE 13

Some tert-butoxycarbonylmethyl polyglutamate prepared according to Example 1 and containing about 20 to 30% of residual moisture after precipitation was used. A solution of 5% by weight of this polymer in PEG-400 was prepared and some films approximately 0.1 to 0.2 mm thick were prepared by pouring the solution over a support (glass plate) and by then washing the support with water (by immersion in a slow stream) for variable periods ranging from 4 hours to 24 hours.

The films thus obtained contained variable quantities of PEG retained in the polymer substance (approximately 0.1 to 5%, depending on the washing time).

These films were soaked in a buffer solution 0.05 M, pH 8.5, ordinary temperature, and it was found that degradation of these films (hydrolysis) varied as a function of the residual PEG content, the minimum time observed (highest PEG content) being 3 hours and the maximum time 48 hours.

The above-mentioned tests were repeated using as degradation medium an aminopeptidase leucine solution containing 8.5 U/ml in a buffer (pH 8.5) 0.1 M borate and 0.005 M $MgCl_2$. Under these conditions, the hydrolysis rates were substantially doubled.

EXAMPLE 14

Dodecyloxycarboxylmethyl polyglutamate 7.00 g (0.0542 moles) of polyglutamic acid were dissolved in 150 ml of DMF. 2 equivalents of tributylamine (TBA) (20 g, 0.108 moles) and 2 equivalents of dodecanyl bromoacetate (33 g, 0.108 moles) prepared by esterification of bromoacetic acid using dodecanol in the presence of dicyclohexylcarbodiimide (DCC) are added. The solution becomes cloudy after 20 minutes. The precipitate is redissolved by adding 50 ml of chloroform then 250 ml of ether. After 5 days of reaction, the reaction mixture is evaporated in a rotavapor to 150 ml and the mixture is precipitated in 1 liter of MeOH. The polymer is redissolved in ether and precipitated by hexane. It is soluble in ethylether, $CH_2Cl_2$, $CHCl_3$, isopropyl myristate, sesame and sunflower oils, ethyl acetate. It is insoluble in DMF, acetone, water, petroleum ether. NMR analysis of the polymer confirms the presence of dodecyl groups. The esterification rate is measured by gaseous phase chromatography of the hydrolysate: 105 mg of polymer are introduced into 7 ml of NaOH 5N for two hours with reflux. The mixture is then acidified to pH 2-3 with 35% HCl; the dodecanol obtained is extracted using 4×15 ml of ether and an aliquot of the mixture is injected into a gaseous phase chromatogram: analysis demonstrates a substitution rate of 51%.

EXAMPLE 15

[poly(oxyethylene)methylether]-oxycarbonylmethyl polyglutamate.

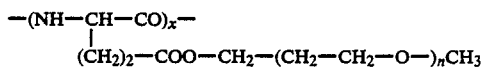

1. Some poly(oxyethylene)monomethyl-ether bromoacetate is firstly prepared in the following manner:

24.6 g (0.177 moles) of bromoacetic acid are dissolved in 200 ml of ethyl acetate. 31 g of polyethyleneglycol 350 (PEG 350, Fluka), n≈8, 1 g of 4-pyrrolidinopyridine are added. The mixture is cooled to −4° C. and 36.5 g of DCC (0.177 moles) dissolved in 100 ml of ethyl acetate are added dropwise. The mixture is filtered after 24 hours, the filtrate is evaporated until production of an oil which is extracted with 5×200 ml of petroleum ether to eliminate the excess bromoacetic anhydride and the 4-pyrrolidinopyridine. The NMR spectrum of the product obtained corresponds to the formula

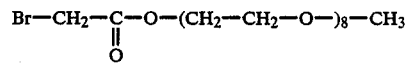

$\sigma = 3.35$ ppm ($OCH_3$) $\sigma = 3.6$ ppm ($CH_2—CH_2—O$) and $\sigma = 3.90$ ppm ($Br—CH_2—CO$).

2. The polymer is prepared by reacting 2 g of PGA with 15 g of polyethyleneglycol monomethylether bromoacetate and 5.6 g of TBA in 75 g of DMF. After 5 days of reaction, the polymer is precipitated with $H_2O$, is redissolved in methanol and is precipitated with ether. The NMR spectrum of the polymer obtained confirms the presence of ethylene oxide residues ($\sigma = 3.6$ ppm) along the polypeptide chain. The polymer is soluble in methanol, acetone, chloroform and the polyethylene glycols. It is insoluble in water, ether and petroleum ether.

The existence of analogous compounds derived directly from PGA, the polyethylene glycol monomethyl polyglutamates, will be noted in the present Example (see Japan Kokai 59-149927). The biodegradability properties of these compounds are not known, however, and, in view of the structure of these compounds, they should be inferior to those of the compounds corresponding to the present invention.

We claim:

1. A polypeptide comprising a member of the group consisting of (a) biodegradable polymers corresponding to the formula

in which $R^1$ is a lower alkyl or hydrogen, R being a substituted or unsubstituted aliphatic radical or aromatic radical; or R and $R^1$ are bound to one another to form a hydrocarbon bridge of two or three links which may or may not be substituted; and (b) polymers corresponding to the formula:

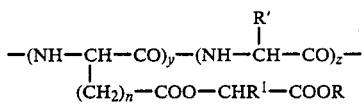

wherein the groups R and R¹ have the meanings given above and wherein

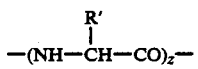

is an uncarboxylated or carboxylated amino acid moiety of which the —COOH is free or partially or completely esterified; n is 1 or 2 and x which is equal to y+z is selected so that the molecular weight of the polypeptide is not less than 5000 D.

2. A polypeptide according to claim 1, characterised in that R is selected from the methyl, ethyl, isopropyl, isobutyl, tert.butyl, neopentyl, phenyl, benzyl radicals, the $C_{10}$ to $C_{22}$ fatty alkyls and methoxylated polyethylene glycol containing from 1 to 100 oxyethylene units.

3. A polypeptide according to claim 1, characterised in that, when R and R¹ are bound to one another, the link formed by them is selected from the following formulae —CH$_2$—CH$_2$—; —CH=CH—; —CH(CH$_3$)—CH(CH$_3$); —C(CH$_3$)=C(CH$_3$)—; 1,2-phenylene; cyclohexenylene; cyclopentenylene, cyclopentadienylene, trimethylene; —CH=CH—CH$_2$—;

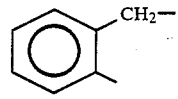

4. A polypeptide according to claim 1, characterised in that the compound I is selected from alkyloxycarbonylmethyl and aryloxycarbonylmethyl glutamate and aspartate, that compound II is selected from the copolymers of alkyloxycarbonylmethyl and aryloxycarbonylmethyl glutamate or aspartate with one or more other amino acids selected from alanine, leucine, valine and phenylalanine.

5. A polypeptide according to claim 1, characterised in that the copolymer II is selected from the copolymers of polyglutamate or asparatate I with glutamic acid and/or the lower alkyl glutamates and aspartic acid and/or the lower alkyl aspartates respectively.

6. A polypeptide according to claim 4, characterised in that the alkyl or aryl groups R are selected from the methyl, ethyl, propyl, isopropyl, butyl, isobutyl, neopentyl, benzyl, phenyl, lauryl, ketyl, oleyl and stearyl groups.

7. A polypeptide according to claim 1 wherein R is a hydroxylated or alkoxylated polyoxyalkylene radical.

* * * * *